United States Patent [19]

Gurvich et al.

[11] Patent Number: 4,961,929

[45] Date of Patent: Oct. 9, 1990

[54] PROCESS OF REPELLING DOGS AND DOG REPELLENT MATERIAL

[75] Inventors: Max A. Gurvich; Robert W. Parent, both of Seattle; Eugene H. Brandli, Issaquah, all of Wash.

[73] Assignee: Pace National Corporation, Kirkland, Wash.

[21] Appl. No.: 541,382

[22] Filed: Oct. 12, 1983

Related U.S. Application Data

[63] Continuation-in-part of Ser. No. 456,205, Jan. 7, 1983.

[51] Int. Cl.$^5$ .............................................. A61K 35/78
[52] U.S. Cl. ...................... 424/196.1; 424/DIG. 10; 514/920; 71/23
[58] Field of Search .................. 424/195, 195.1, 196.1; 514/920

[56] References Cited

U.S. PATENT DOCUMENTS 3,923,997 12/1975 Meuly ................................. 424/279
4,353,896 10/1982 Levy .................................. 424/195

OTHER PUBLICATIONS

The Merck Index, 9th Ed., 1976, pp. 510, 511, 798 and 969.

*Primary Examiner*—John W. Rollins
*Attorney, Agent, or Firm*—Robert W. Beach; Ward Brown

[57] ABSTRACT

The process of utilizing as a dog repellent, such as in a semiliquid slug bait or as a spray or as an impregnant or as a fertilizer component, material selected from the group consisting of methyl salicylate, birch oil, wintergreen oil, eucalyptus oil, pine oil and pine-needle oil.

12 Claims, No Drawings

PROCESS OF REPELLING DOGS AND DOG REPELLENT MATERIAL

RELATED APPLICATION

This application is a continuation-in-part of patent application Ser. No. 456,205, filed Jan. 7, 1983, of Max A. Gurvich and Robert W. Parent, for Thick Suspension Bait.

BACKGROUND OF THE INVENTION

1. Field of the Invention

This invention relates to a process for repelling dogs and dog repellent material used in such process.

2. Prior Art

In the past where access of a dog to a particular object or material was not desired, either to protect the object or to protect the dog, or both, the usual technique has been to prevent access of the dog to the object or material physically, such as by confining or limiting the range of the dog or by enclosing the object or material. The latter expedient has been the only practical solution for dogs not owned by the owner or user of the object or material.

A specific problem has occurred in attempting to prevent stray dogs from eating poison bait.

SUMMARY OF THE INVENTION

A principal object of the present invention is to provide a bait pesticide, particularly for slugs, snails, insects and rodents, which is potent as such a bait but which will not endanger dogs.

More specifically, it is an object to provide such a bait which will not be attractive to dogs and which in fact will repel dogs.

A companion object is to provide a dog repellent material which can be used in environments other than bait for the purpose of repelling dogs from other material and objects.

The foregoing objects can be achieved by utilizing in the material which it is desired to be unattractive to dogs, or in connection with objects which it is desired to have dogs avoid, a dog repellent material selected from the group consisting of methyl salicylate, eucalyptus oil and pine oil and pine-needle oil.

DETAILED DESCRIPTION

THE PROBLEM

As applied to pesticides and bait, the problem addressed by the present invention was to provide bait in the physical form and containing poison which would be most effective for eliminating slugs, snails, insects and/or rodents, which at the same time would not be disturbed or removed by dogs, and particularly which would not be eaten by dogs to their detriment. Providing a solution to such problem could follow any one of several courses.

A first course that could be followed would be to utilize in the bait a poison which would be effective to eliminate the type of pest for which it was intended but which would be harmless or substantially harmless to dogs. The problem could not be solved easily by such an expedient, however, because of the difficulty of finding a poison which would be deadly to one or more categories of pests while being substantially innocuous to dogs.

A second possible solution would be to provide bait having a physical character which would not be attractive to dogs but which would provide an effective vehicle for pesticide. The present invention was particularly concerned with a bait which may be semiliquid or dry especially effective in the elimination of slugs and snails, which was not particularly attractive to dogs yet which was not so devoid of appeal that it would be shunned by all dogs.

To be an effective pesticide a bait must have an attractant that will lure slugs, snails and/or other pests to the bait, but it has been difficult to find such an attractant which had no appeal whatever to dogs.

Another technique would be to incorporate in the pesticide a material which would not repel the pests for which the bait was intended, but which would repel dogs to such an extent that virtually no dogs would bother the bait. In order to provide such a solution for the problem, however, it was necessary to find a material which would have properties repellent to dogs but which would not repel pests.

The Solution

Of the various possible types of solutions discussed above the present invention relates to the use of a material either in pesticide bait, or in other ways, which repels dogs but which does not appreciably repel pests such as slugs and snails.

The substances found to be dog repellents while not repelling slugs are pine oil, pine-needle oil, eucalyptus oil and methyl salicylate. Methyl salicylate is a liquid ester having the formula $HOC_6H_4COOCH_3$, which may be in the form of a synthetic material or in the natural content of birch oil or sweet birch oil extracted from the bark or twigs of birch or sweet birch trees, or wintergreen oil or gaultheria oil obtained from the macerated leaves of wintergreen. Pine oil, pine-needle oil, eucalyptus oil, birch oil and wintergreen oil are all essential oils.

Pine oil may be any of various oils obtained from pines or other conifers or oils similar to such oils in composition which are colorless to light amber liquid with an aroma of pine that contains principally terpineols and other terpenoid alcohols and is obtained from wood, especially of the longleaf pine, and boils at a temperature higher than wood turpentine. Alternatively, the oil can be obtained from the needles and twigs of various pines or other conifers, which oil may be designated pine-needle oil.

Eucalyptus oil can be any of various oils obtained from the leaves of various eucalyptus.

UTILIZATION

A specific process for utilizing the dog repellent materials specified above is in a semiliquid poisonous bait for slugs, snails, insects and rodents. The dog repellent material may be utilized in such bait in proportions from one-tenth percent by weight to one percent or more by weight, but an amount greater than one percent is not necessary to effectively repel dogs. Such bait incorporates a food ingredient as an attractant, such as vegetable, grain, fruit, animal or fowl meat, or fish or a derivative of one or more of such products. The amount of attractant can be from one percent to twenty percent of the bait by weight and where an adequate amount of dog repellent material is used, the amount of attractant in the bait need not be reduced below an amount which will be effective to attract slugs, for example.

The poison in the slug and snail bait can be metaldehyde in the amount of 2 percent to 20 percent of the bait by weight.

For a rodenticide, the poison can be selected from the following examples which can be utilized in proportions from 2 percent to 20 percent by weight:
  zinc phosphide;
  warfarin;
  diphacinone; and
  chlorophacinone.

For insect bait the poison can be Mesurol in the amount of 0.75 percent to 4 percent of the bait by weight or carbaryl - 1-naphthyl N-methylcarbamate in the amount of 2 percent to 10 percent of the bait by weight. All such poisons would be harmful to dogs if eaten in any substantial quantity.

The poison for the slug and snail bait is an insoluble powder which will be suspended in the carrier. The bait also includes an oleaginous base which is an aliphatic hydrocarbon, and the preferred type is paraffinic oil having little odor. Such oil may be mineral oil or white mineral oil. The amount of such oil will range from 5 percent to 15 percent of the bait by weight.

The slug and snail bait also includes an emulsifier which stabilizes the suspension by keeping the oleaginous base suspended in water, and such emulsifier may be nonionic or anionic, or may be a volatile amine soap. The nonionic emulsifier may be ethoxylated nonyl phenol, ethoxylated octyl phenol, polyoxyethylene sorbitan esters such as polyoxyethylene sorbitan stearate, polyoxyethylene sorbitan acetate and polyoxyethylene sorbitan propionate, or polyoxyethylene glycol esters such as polyoxyethylene glycol dioleate, polyoxyethylene glycol sorbitan monooleate, polyoxyethylene glycol sorbitan trioleate, polyoxyethylene glycol stearate, polyoxyethylene glycol acetate and polyoxyethylene glycol propionate. The preferred range for the nonionic emulsifier is 1 percent to 3 percent of the bait by weight. The anionic emulsifier may be phosphated octyl phenol ethoxylate, phosphated nonyl phenol ethoxylate or phosphated fatty alcohol ethoxylate. Such an anionic emulsifier should be used in combination with a nonionic emulsifier. The quantity of such an anionic emulsifier would be preferably 1 percent to 2 percent of the bait by weight. Volatile amine emulsifying soap is produced by the reaction of a volatile amine, such as ammonia or morpholine, with fatty acid having a chain length ranging from 15 to 22 carbon atoms. Suitable fatty acids may be either a saturated acid, such as stearic acid, or an unsaturated acid, such as oleic acid or tall oil, but it is preferred that a blend of saturated and unsaturated fatty acids be used. Such a blend may be produced by mixing saturated and unsaturated acids in a ratio of from one to three parts of unsaturated acid for each part of saturated acid, or a natural blend of saturated and unsaturated fatty acids such as found in soya oil may be used. The total proportion of fatty acid in the bait can vary from 0.5 percent to 7 percent of the bait by weight. The amine content for reaction with the fatty acid to produce amine soap should be within the range of 0.5 percent to 2 percent by weight.

To thicken the suspension to the desired viscosity, such as a substantially homogeneous semiliquid suspension having the consistency of thick mud, the thickener can be alginate, silica, cellulose, gum, starch, glycogen or dextrin or a combination of such thickeners. The silica may be fused silica, talc or magnesium aluminum silicate in powder form. The cellulose may be methyl cellulose, carboxymethyl cellulose or hydroxyethyl cellulose. The gum may be xanthan gum or other polysaccharide gum. The starch may be cornstarch, potato starch, soya starch, rice starch or wheat starch. The nonstarch thickener will be in the range of 0.5 percent to 3 percent of the bait by weight. The starch thickener may be in the range of 2 percent to 10 percent of the bait by weight.

A representative formula for a dog repellent slug and snail bait in which the ingredients are listed by weight is

| | |
|---|---|
| Poison | 2.00% to 20.00% |
| Oleaginous base | 5.00% to 15.00% |
| Emulsifier | 0.50% to 7.00% |
| Nonstarch thickener | 0.50% to 3.00% |
| Starch thickener | 2.00% to 10.00% |
| Attractant | 1.00% to 20.00% |
| Dog repellent | 0.10% to 1.00% |
| Balance - water | |

A specific exemplary formula specifying the ingredients by weight for the semiliquid suspension slug and snail bait having the consistency of thick mud is

| | |
|---|---|
| Metaldehyde | 5.00% |
| White mineral oil | 12.00% |
| Polyoxyethylene sorbitan stearate emulsifier | 2.00% |
| Sodium alginate thickener | 0.90% |
| Wheat starch thickener | 4.00% |
| Attractant | 18.00% |
| Methyl salicylate | 0.50% |
| Water | 57.60% |

In preparing the bait the oleaginous base dog repellent and emulsifier are warmed and mixed to form a homogeneous liquid. The poison, thickener and attractant are then dispersed in such liquid by a rapid, high shear mixing operation. Warm water is added slowly to the blended liquid while it is being agitated to form a suspension. The thickener dispersed in part of the water is added to the suspension to thicken the bait composition to the desired viscosity, which preferably is about 7,000 to 17,000 cp.

OTHER APPLICATIONS

While the principal use of the dog repellent is considered to be in a bait for slugs and snails of the type described above, the dog repellent has utility in other applications alone or in combination with other materials. Thus the repellent material may be incorporated in a semiliquid carrier of the type used for the baits described above but without the poison or the attractant.

Alternatively, the dog repellent can be incorporated in an aqueous emulsion or in a nonaqueous liquid and applied from a container under pressure, or by other conventional sprayers, as a spray to objects which it is desired to have shunned by dogs, such as shrubbery, trees, posts and garbage cans. To prolong the effectiveness of the dog repellent for such applications, cloth tapes can be impregnated with a nonaqueous dog repellent liquid or an emulsified aqueous liquid, and pieces of tape impregnated with such liquid can be hung as streamers adjacent to objects from which it is desired to ward off dogs.

The dog repellent could also be incorporated in other products of granular or liquid form. A further specific product would be use of synthetic methyl salicylate, birch oil, wintergreen oil, eucalyptus oil, pine oil or pine-needle oil in fertilizer used on flower or vegetable gardens to deter dogs from digging up such gardens or defecating in such gardens.

A specific product in the form of a cream which can be dispensed from a tube has the following ingredients by weight:

| Ingredient | Weight % |
| --- | --- |
| Acrylic polymeric thickner adjusted to neutral pH | 1.00% |
| Alkali, for example potassium hydroxide | 0.70% |
| Methyl salicylate | 2.00% to 5.00% |
| Cetyl alcohol | 0.10% |
| Balance water | |

The thickener, alkali, methyl, salicylate and cetyl alcohol are mixed together and stirred into the water.

We claim:

1. The process of repelling dogs from a selected location which comprises applying in the area of the location a composition containing material selected from the group consisting of pine oil and pine-needle oil.

2. The process of repelling dogs from a selected location which comprises applying in the area of the location a semiliquid composition containing material selected from the group consisting of pine oil and pine-needle oil.

3. The process of repelling dogs from a selected location which comprises spraying on the area of the location a liquid containing material selected from the group consisting of pine oil and pine-needle oil.

4. In a process of making a dog repelling composition, the improvement which comprises scenting the composition with material selected from the group consisting of methyl pine oil and pine-needle oil.

5. Slug and snail bait comprising poison, an attractant, and a thickener selected from the group consisting of alginate, silica, cellulose, gum, starch, glycogen and dextrin to form a substantially homogeneous semiliquid suspension having the consistency of thick mud.

6. A dog repellant composition comprising a substantially homogeneous semiliquid suspension having the consistency of thick mud and containing dog-repelling material selected from the group consisting of pine oil and pine-needle oil.

7. The composition defined in claim 6, incorporating the dog repellent in an amount of one-tenth to one percent by weight of the composition.

8. In a composition containing an ingredient potentially harmful to dogs, the improvement comprising the composition containing a dog repelling ingredient selected from the group consisting of pine oil and pine-needle oil.

9. In the composition defined in claim 8, the composition containing dog repelling ingredient in the amount of one-tenth to five percent of the composition by weight.

10. An improved soil fertilizing composition comprising fertilizer incorporating dog repelling material selected from the group consisting of
   pine oil and
   pine-needle oil.

11. A dog repelling product comprising a container fluid confined in said container under pressure, said fluid being scented with dog repelling material selected from the group consisting of pine oil and pine-needle oil, and means for dispensing the scented fluid from said container.

12. A dog repelling product comprising a dispensing tube and a cream confined in the tube and scented with dog repellent material selected from the group consisting of pine oil and pine-needle oil.

* * * * *